US011857480B1

(12) United States Patent
Wu (10) Patent No.: US 11,857,480 B1
(45) Date of Patent: Jan. 2, 2024

(54) SEXUAL STIMULATION DEVICE (71) Applicant: Junpeng Wu, Shenzhen (CN)

(72) Inventor: Junpeng Wu, Shenzhen (CN)

(*) Notice: Subject to any disclaimer, the term of this patent is extended or adjusted under 35 U.S.C. 154(b) by 0 days.

(21) Appl. No.: 18/123,970

(22) Filed: Mar. 20, 2023

(30) Foreign Application Priority Data

Mar. 8, 2023 (CN) .......................... 202310245770.1

(51) Int. Cl.
*A61H 19/00* (2006.01)
*A61H 21/00* (2006.01)
*A61H 23/02* (2006.01)
*A61F 5/41* (2006.01)

(52) U.S. Cl.
CPC ............. *A61H 19/50* (2013.01); *A61H 19/32* (2013.01); *A61H 19/34* (2013.01); *A61H 19/40* (2013.01); *A61H 21/00* (2013.01); *A61F 2005/414* (2013.01); *A61H 23/02* (2013.01); *A61H 2201/10* (2013.01); *A61H 2201/163* (2013.01); *A61H 2201/165* (2013.01)

(58) Field of Classification Search
CPC ........ A61H 19/50; A61H 19/32; A61H 19/34; A61H 19/40; A61H 21/00; A61H 23/02; A61H 2201/10; A61H 2201/163; A61H 2201/165; A61F 2005/414
USPC ..................................................... 600/38–41
See application file for complete search history.

(56) References Cited

U.S. PATENT DOCUMENTS

| 10,940,078 B1 * | 3/2021 | Lee .......................... A61H 19/34 |
| 2009/0069629 A1 * | 3/2009 | Uson Calvo ........... A61H 19/34 600/38 |
| 2010/0010292 A1 * | 1/2010 | Talbot ................. A61H 23/0263 600/38 |
| 2013/0296645 A1 * | 11/2013 | Evans ..................... A61H 19/40 600/41 |
| 2015/0174001 A1 * | 6/2015 | Milton ................... A61H 19/50 600/41 |
| 2016/0279019 A1 * | 9/2016 | Callow .................. A61H 19/44 |
| 2017/0273861 A1 * | 9/2017 | Page ...................... A61H 19/32 |
| 2017/0360653 A1 * | 12/2017 | Marshall ................ A61H 21/00 |
| 2020/0368103 A1 * | 11/2020 | Rakshit .................. A61H 19/50 |
| 2022/0395426 A1 * | 12/2022 | Myerson ................ A61H 19/44 |

FOREIGN PATENT DOCUMENTS

WO WO-2009087627 A2 * 7/2009 ............. A61H 19/30

OTHER PUBLICATIONS

Doc Johnson "KINK—Dual-Flex Silicone Vibrator with Wireless Remote" https://web.archive.org/web/20200921101245/https://docjohnson.com/kink-dualflex-siliconevibratorwith-wirelessremote.html; accessed online on Sep. 26, 2023 (Year: 2020).*

* cited by examiner

Primary Examiner — Kaylee R Wilson (57) ABSTRACT

A sexual stimulation device includes a ring structure, at least one first function member, at least one second function member and at least one battery. The ring structure has two opposite sides. The first function member is positioned at one side of the ring structure. The second function member is positioned at the other side of the ring structure. The battery is arranged in the first function member and/or the second function member. The first function member and the second function member collectively include N stimulation sources, wherein N is greater than or equal to 3.

17 Claims, 12 Drawing Sheets

SEXUAL STIMULATION DEVICE

CROSS-REFERENCE TO RELATED APPLICATIONS

This application claims priority to Chinese Patent Application No. 202310245770.1 filed on Mar. 8, 2023, the entire contents of which are hereby incorporated by reference.

TECHNICAL FIELD

The present invention relates to the technical field of stimulation devices, and more particularly to a sexual stimulation device.

DESCRIPTION OF THE PRIOR ART

Various sexual stimulation devices are commercially available to males or females. These devices include manually driven products or electrical products, each of which is used to stimulate a specific part at a certain time. These devices have a relatively single function and a poor user experience. Some devices are complicated to use and need to be worn and used by using components such as bandages.

SUMMARY OF THE DISCLOSURE

An object of an embodiment of the present invention is to provide a sexual stimulation device which is simple to operate and capable of providing stimulation to both sexual partners.

In order to achieve the above-mentioned object, a technical solution adopted by the present invention is to provide a sexual stimulation device, including:
   a ring structure;
   at least one first function member positioned at one side of the ring structure;
   at least one second function member positioned at the other side of the ring structure; and
   at least one battery arranged in the first function member and/or the second function member,
   wherein the first function member and the second function member collectively include N stimulation sources, and wherein N is greater than or equal to 3.

The sexual stimulation device provided by the present invention has the following beneficial effects that compared with the prior art, the sexual stimulation device of the present invention is provided with the ring structure allowing for inserting of the finger or the penis without fixed components such as bandages, thereby being simple in overall structure and convenient to wear and operate. After a male partner wears the sexual stimulation device, the penis is inserted into the ring structure, which can effectively prolong the sexual duration. The first function member can stimulate the clitoris and/or the vagina. The second function member can stimulate the testis and/or the perineum and/or the anus. Accordingly, the sexual stimulation device can provide stimulation sensations to the male partner and the female, which increases the sexual interest. The sexual stimulation device is provided with N stimulation sources. Users can turn on or off the corresponding stimulation sources according to their own needs, thereby providing the users with more choices and enriching the use functions of the device.

BRIEF DESCRIPTION OF DRAWINGS

In order to more clearly explain technical solutions in embodiments of the present invention, accompanying drawings required to be used in the embodiments or the description of the prior art will be briefly introduced below. Apparently, the accompanying drawings in the following description are only some embodiments of the present invention. For those ordinarily skilled in the art, other accompanying drawings can be obtained from these accompanying drawings without paying any creative labor.

FIG. 8 is a cross-sectional view of the sexual stimulation device shown in FIG. 7;

DESCRIPTION OF EMBODIMENTS

In order to make technical problems, technical solutions and beneficial effects to be solved in the present invention clearer, the present invention will be further described below in detail in conjunction with accompanying drawings and embodiments. It should be understood that specific embodiments described herein are only used to explain the present invention and not to limit the present invention.

It should be noted that when an element is referred to as "fixed to" or "arranged on" another element, it can be directly or indirectly on another element. When an element is referred to as "connected to" another element, it can be directly or indirectly connected to another element.

It should be understood that the orientational or positional relationship indicated by terms "length", "width", "up", "down", "front", "back", "left", "right", "vertical", "horizontal", "top", "bottom", "inside", "outside", and the like is based on the orientational or positional relationship shown in the accompanying drawings, and is only for the sake of describing the present invention and simplifying the description instead of indicating or implying that the apparatus or element referred to must have a specific orientation, and must be constructed and operated in a specific orientation, so it cannot be understood as a limitation of the present invention.

Also, terms "first" and "second" are only used for describing purposes, and cannot be understood as indicating or implying relative importance or implying the number of technical features indicated. Therefore, features defined with "first" and "second" can explicitly or implicitly include one or more of these features. In the description of the present invention, "a plurality of" means two or more, unless otherwise specified.

Now, referring to FIG. 1 to FIG. 4 together, the sexual stimulation device provided by an embodiment of the present invention will be described. The sexual stimulation device includes a ring structure 100, at least one first function member 200, at least one second function member 300 and at least one battery 311. The ring structure 100 is annular and elastic, and allows for inserting of the penis or the finger. After the penis or the finger is inserted into the ring structure 100, the ring structure 100 may be tightly mounted around the penis or the finger. With the ring structure 100 mounted around the penis, the sexual duration may be prolonged.

Figure 1:
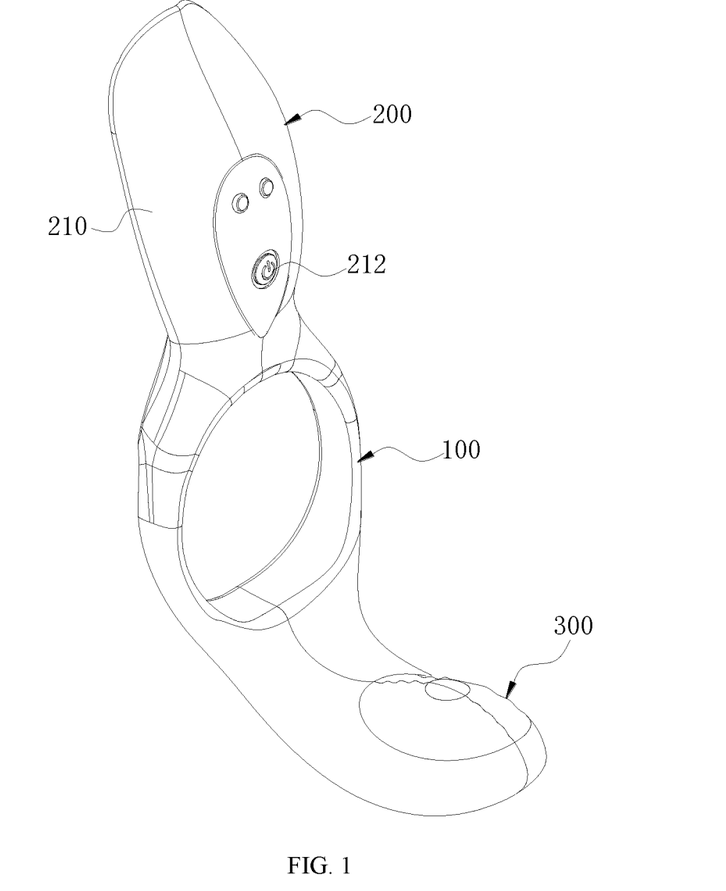
FIG. 1 is a perspective view showing a sexual stimulation device in accordance with an embodiment of the present invention.

The ring structure 100 has two opposite sides. The at least one first function member 200 is arranged on one side of the ring structure 100. The at least one second function member 300 is arranged on the other side of the ring structure 100. When the sexual stimulation device is used, the first function member 200 can stimulate the clitoris and/or the vagina, and the second function member 300 can stimulate the perineum and/or the anus and/or the testis. As shown in FIG. 1, one first function member 200 is arranged above the ring structure 100, and used to stimulate the clitoris and/or the vagina of the female partner. One second function member 300 extending backwards is arranged at a bottom side of the ring structure 100, and used to stimulate the perineum and/or the anus and/or the testicles of the male partner. In other embodiments, the second function member 300 may extend forwards, and thus can stimulate the perineum and/or the anus of the female partner.

The number of the batteries 311 may be one or more. The battery 311 is arranged within the first function member 200 and/or the second function member 300. The first function member 200 and the second function member 300 have a total of N stimulation sources, and N is greater than or equal to 3. The battery 311 can supply power to each stimulation source. That is, the first function member 200 is provided with at least one stimulation source, the second function member 300 is provided with at least one stimulation source, and the number of the stimulation sources provided by the first function member 200 and the second function member 300 is greater than or equal to 3.

The stimuli provided by the N stimulation sources include at least one of mechanical stimulus, electrical stimulus and heating stimulus. The stimuli provided by the first function member 200 include at least one of mechanical stimulus, electrical stimulus and heating stimulus. The stimuli provided by the second function member 300 include at least one of mechanical stimulus, electrical stimulus and heating stimulus. The mechanical stimulus is at least one of vibrating, swinging, twisting, buckling, slapping, extending-retracting and suctioning. A mode selection key may be arranged on the corresponding function member, and a user can select a corresponding mode according to his or her needs to obtain one of the mechanical stimulus or multiple mechanical stimuli that may be automatically on/off keyed. The electrical stimulus may be stimulus on the skin by micro-currents. The heating stimulus may be formed by heating to a preset temperature or gradually heating. The stimuli provided by the first function member 200 and the stimuli provided by the second function member 300 may be the same or different. When the first function member 200 and the second function member 300 each have multiple stimuli, some stimuli of the first and second function members 200, 300 may be the same, and some stimuli of the first and second function members 200, 300 may be different. When the user uses the sexual stimulation apparatus, all or part of the stimulation functions may be energized, which provides the user with more choices and different experiences.

Compared with the prior art, the sexual stimulation device of the present invention is provided with the ring structure allowing for inserting of the finger or the penis without fixing components such as bandages, thereby being simple in overall structure and convenient to wear and operate. After the male partner wears the sexual stimulation device, the penis is inserted into the ring structure 100, which can effectively prolong the sexual duration. The first function member 200 can stimulate the clitoris and/or the vagina. The second function member 300 can stimulate the testis and/or the perineum and/or the anus. Accordingly, the sexual stimulation device can provide stimulations to the male partner and the female, which increases the sexual interest. The sexual stimulation device is provided with N stimulation sources. Users can turn on or off the corresponding stimulation sources according to their own needs, thereby providing the users with more choices and enriching the use functions of the device.

The ring structure 100 can adopt a single-ring structure or a multi-ring structure. When the ring structure adopts the multi-ring structure, the number of the ring structures may be two or more. The first function member 200 is provided with a first on/off key 212, which can at least control the On or Off of the stimulation sources provided by the first function member 200. In some embodiments, the first on/off key 212 can control the On or Off of all the stimulation sources.

Referring to FIG. 1 to FIG. 4, in this embodiment, the ring structure 100 adopts the single-ring structure. The at least one second function member 300 of the sexual stimulation device includes a proximal second function member 310 connected to the ring structure 100. The proximal second function member 310 extends backwards to stimulate the male partner's perineum and the testis. When a male partner wears the sexual stimulation device, the proximal second function member 310 abuts against the perineum of the male partner, thereby stimulating the male partner's perineum and the testicles. Arc-shaped ribs are provided on a top surface of one end of the proximal second function member 310 away from the ring structure 100. A heating device may be arranged within the proximal second function member 310, and a temperature change can be generated by the heating device, which can stimulate the perineum of the male partner. In other embodiments, the proximal second function member 310 may extend forwards, and thus can stimulate the perineum of the female partner.

Figure 3:
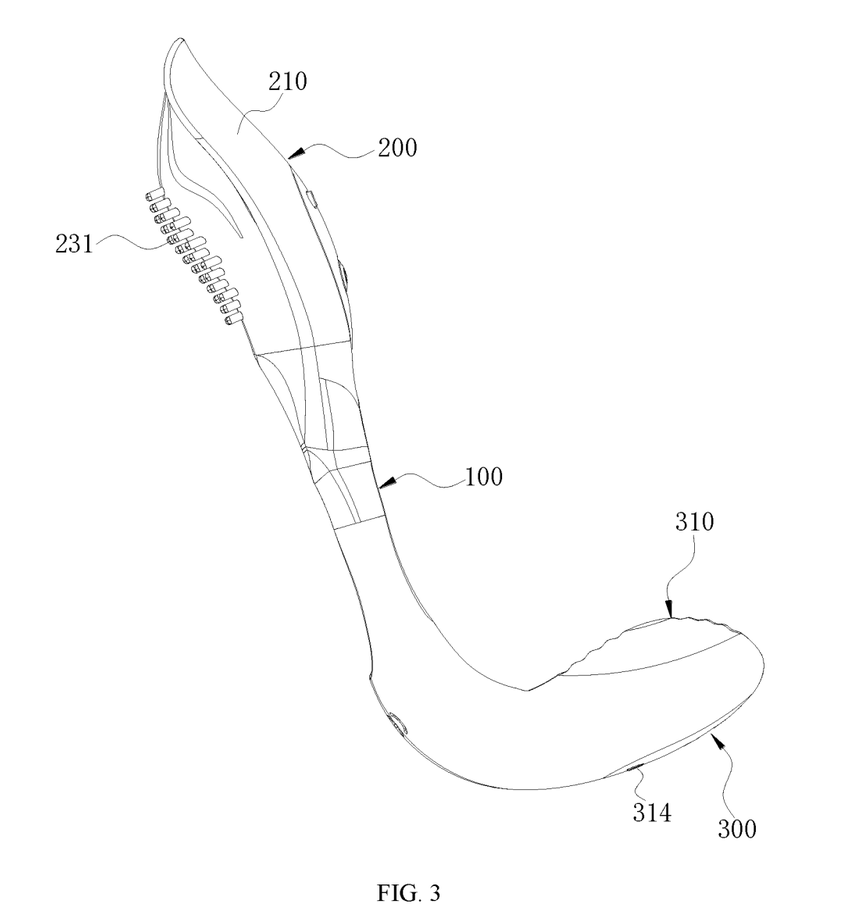
FIG. 3 is a side view of the sexual stimulation device shown in FIG. 1.
Figure 4:
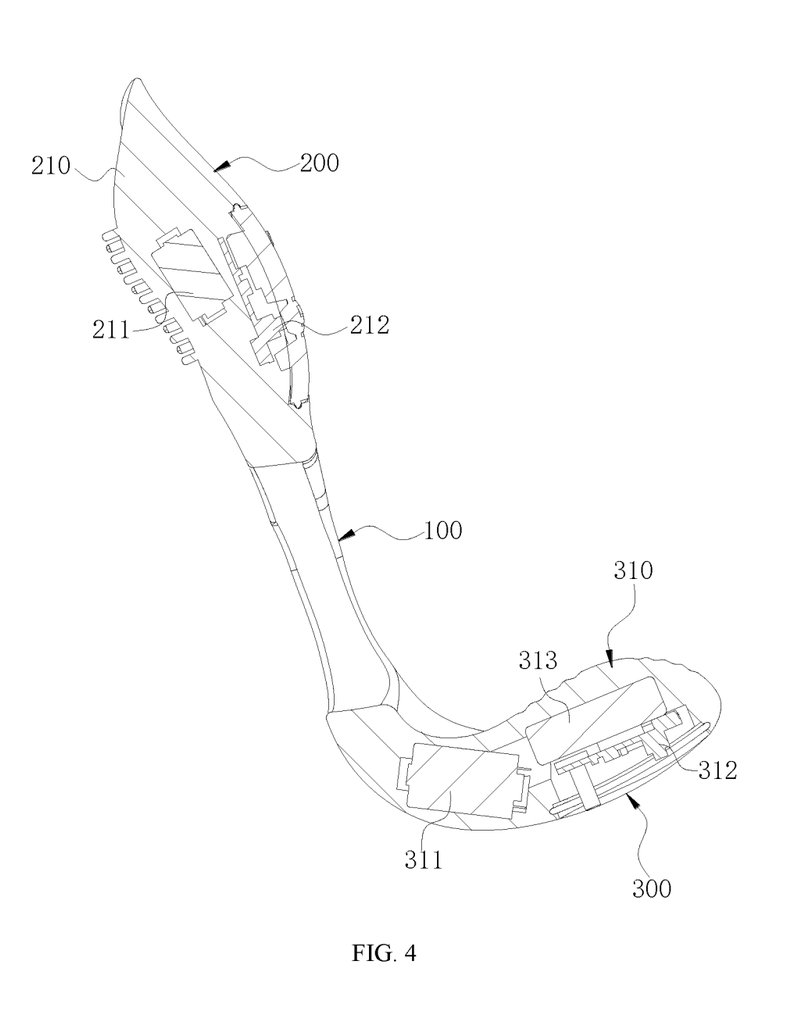
FIG. 4 is a cross-sectional view of the sexual stimulation device shown in FIG. 1.

Referring to FIG. 1, FIG. 3 and FIG. 4, the at least one first function member 200 includes a proximal first function member 210 connected to the ring structure 100. A first vibration stimulation source 211 is arranged within the proximal first function member 210, and a third vibration stimulation source 311 is arranged within the proximal second function member 310. The first vibration stimulation source 211 and the third vibration stimulation source 311 may both include motors. A plurality of motors may be arranged within the proximal first function member 210, and a plurality of motors may be arranged within the proximal second function member 310. It should be understood that when proximal the second function member 310 is short, the proximal second function member 310 can stimulate the testis. When the proximal second function member 310 is long, the proximal second function member 310 can stimulate the testis and the perineum.

A first circuit board 212 is arranged within the proximal first function member 210. The first vibration stimulation source 211 is electrically connected to the first circuit board 212. The first circuit board 212 includes a program to implement a vibration mode. A second circuit board 312 is arranged within the proximal second function member 310. The third vibration stimulation source 311 is electrically connected to the second circuit board 312. The second circuit board 312 includes a program to implement a vibration mode. A first on/off key 212 is arranged on a rear wall of the proximal first function member 210 to turn on or off the first vibration stimulation source 211. In some embodiments, the first on/off key 212 can turn on the first vibration source 211 and the second vibration source 221 in more than one mode. In this embodiment, the second on/off key 314 is arranged at a bottom of the second function member 300 to turn on or off the third vibration stimulation source 311. A battery 313 is arranged within the second function member 300, and a charging port is arranged at a position corresponding to the battery 313. The first circuit board 212 and the second circuit board 312 share the same battery 313. It should be understood that only one on/off key may be provided on the proximal first function member 210 or the proximal second function member 310 to control the On or Off of the first vibration stimulation source 211 and the second vibration stimulation source 221.

Figure 2:
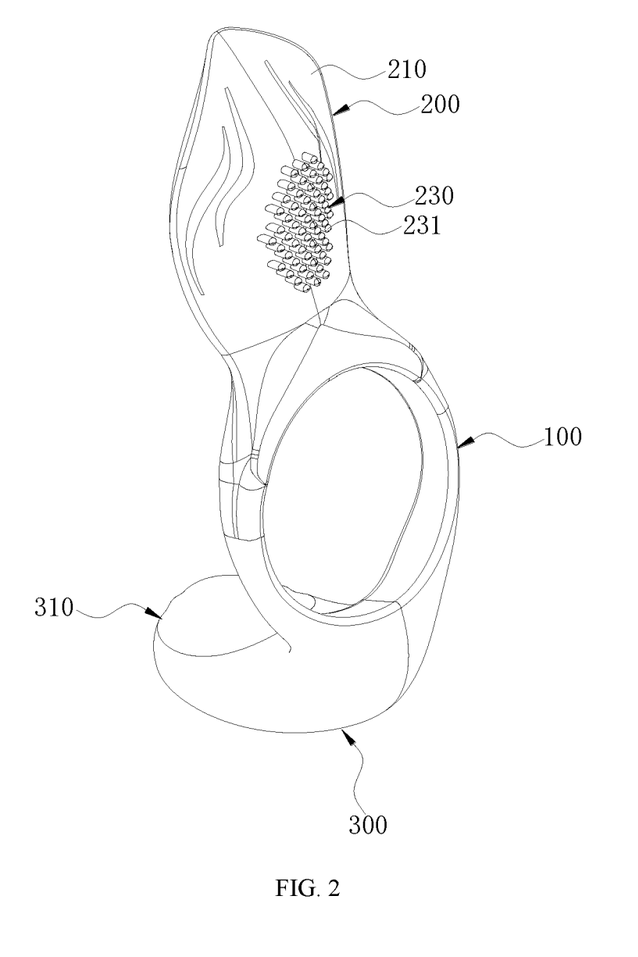
FIG. 2 is a perspective view of the sexual stimulation device shown in FIG. 1, viewed from another aspect.

Referring to FIG. 2 to FIG. 4, a protrusion 230 is arranged on a front side wall of the proximal first function member 210, and may include multiple ribs or multiple bulges. After the man wears the sexual stimulation device, the protrusion on the front side of the proximal first function member 210 abuts against the clitoris of the female partner and the area around the clitoris. In this way, the protrusion 230 can massage the clitoris after the first vibration stimulation source 210 is turned on. In an embodiment, the protrusion 230 includes a plurality of ribs on the front side wall of the proximal first function member 210, and the ribs may be arc-shaped or spiral. In this embodiment, the protrusion 230 includes a plurality of bulges 231 protruding from the front side wall of the proximal first function member 210. The front ends of the bulges 231 all are of a dome structure. As such, the bulge 231 will not scratch the skin of the female partner, and can provide a more comfortable massage stimulus.

The proximal first function member 210 has a width greater than or equal to its thickness. In this way, the proximal first function member 210 has a larger width. When the sexual stimulation device is used, the contact area between the proximal first function member 210 and the clitoris and the skin around the clitoris is larger, which can improve the stimulation effect.

Figure 5:
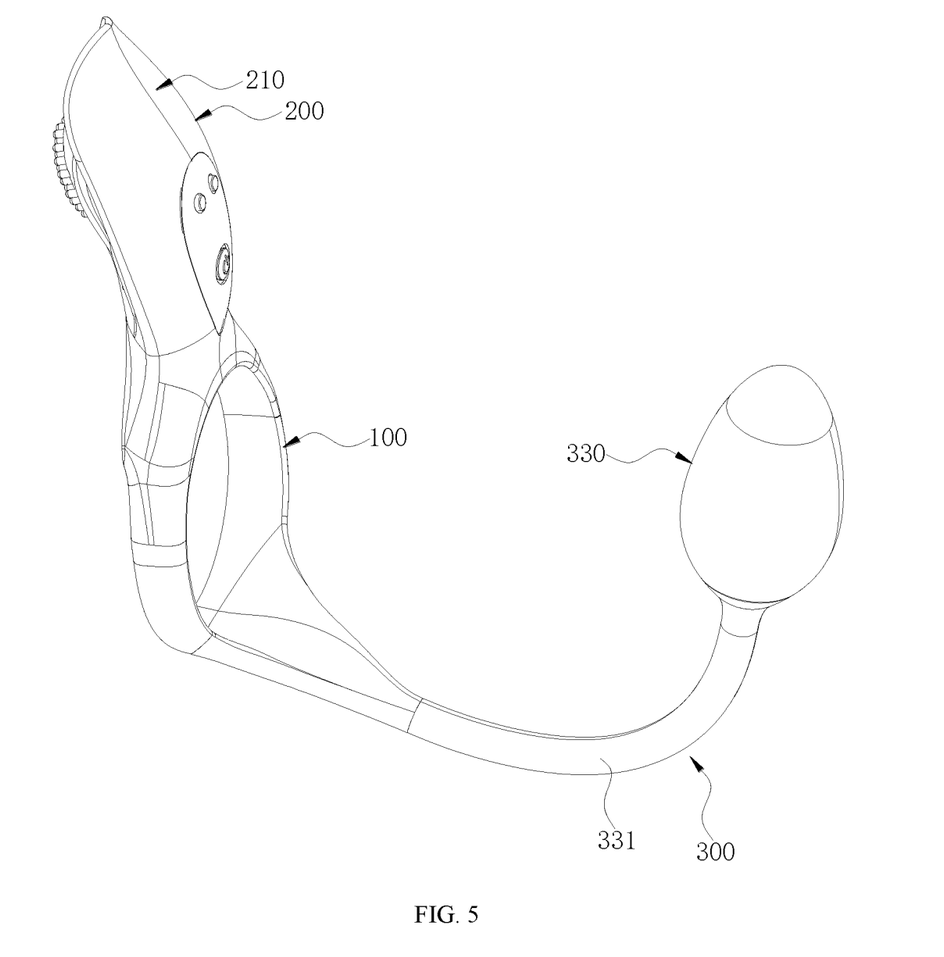
FIG. 5 is a perspective view showing a sexual stimulation device in accordance with another embodiment of the present invention.
Figure 6:
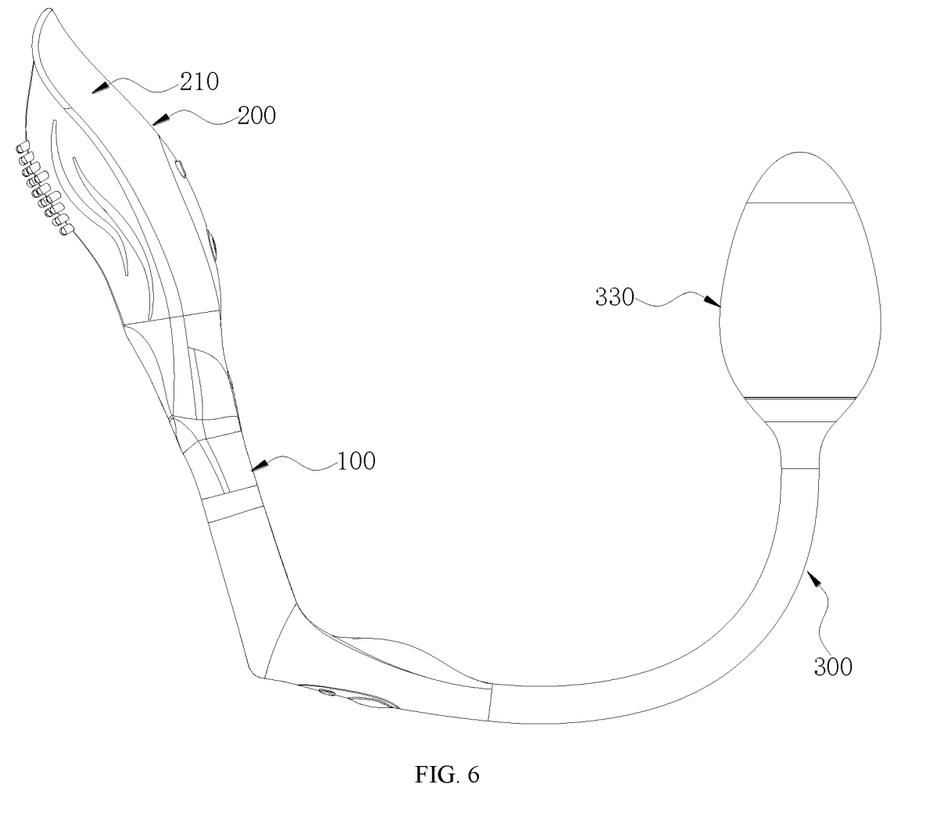
FIG. 6 is a side view of the sexual stimulation device shown in FIG. 5.

Referring to FIG. 5 and FIG. 6, in this embodiment, the ring structure 100 adopts the single-ring structure. The second function member 300 of the sexual stimulation device includes an anal plug 330. The anal plug 330 is provided with at least one stimulation source. The anal plug 330 is suitable for inserting into the anus of the male partner to stimulate the anus. The anal plug 330 may be of a shape of a water drop with a small and smooth top, which brings the convenience for inserting into the anus. The anal plug 330 is connected to the ring structure 100 through a connecting member 331 extending from a front side to a rear side. A width of an adjoining part of the connecting member 331 adjacent to the ring structure 100 gradually decreases from a joint to the ring structure 100 in the extension direction, that is, the adjoining part of the connecting member 331 has a larger width at the joint between the connecting member 331 and the ring structure 100 and the width is gradually reduced, such that the joint has a greater structural strength. The remaining part of the connecting member 331 is of an elongated and curved column shape, which facilitates to extending from the perineum to the anus of the male partner. A heating device may be arranged within the anal plug 330, and a temperature change may be generated by the heating device, which stimulate the anus of the male partner. It should be understood that when the second function member 300 extends forwards, the anal plug 330 can stimulate the anus of the female partner.

Figure 7:
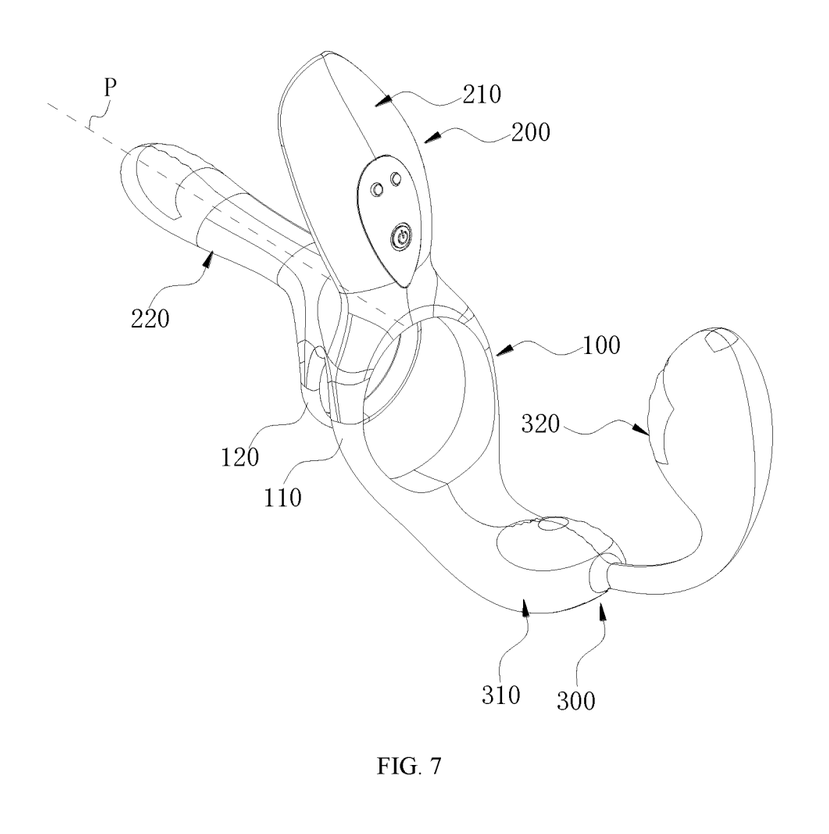
FIG. 7 is a perspective view showing a sexual stimulation device in accordance with a further embodiment of the present invention.
Figure 8:
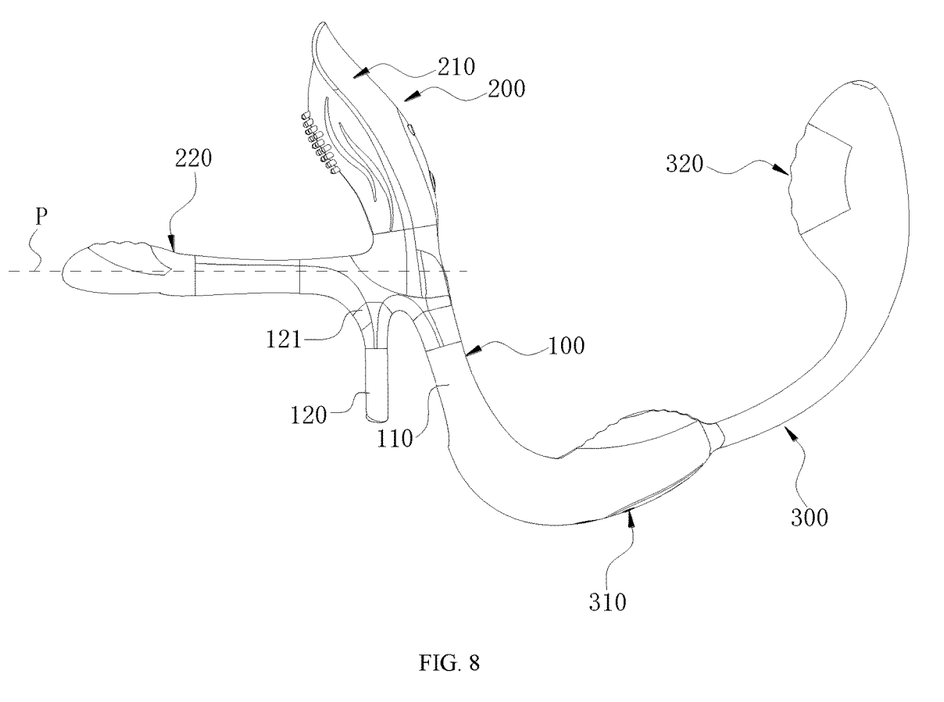
FIG. 8 is a side view of the sexual stimulation device shown in FIG. 7.
Figure 9:
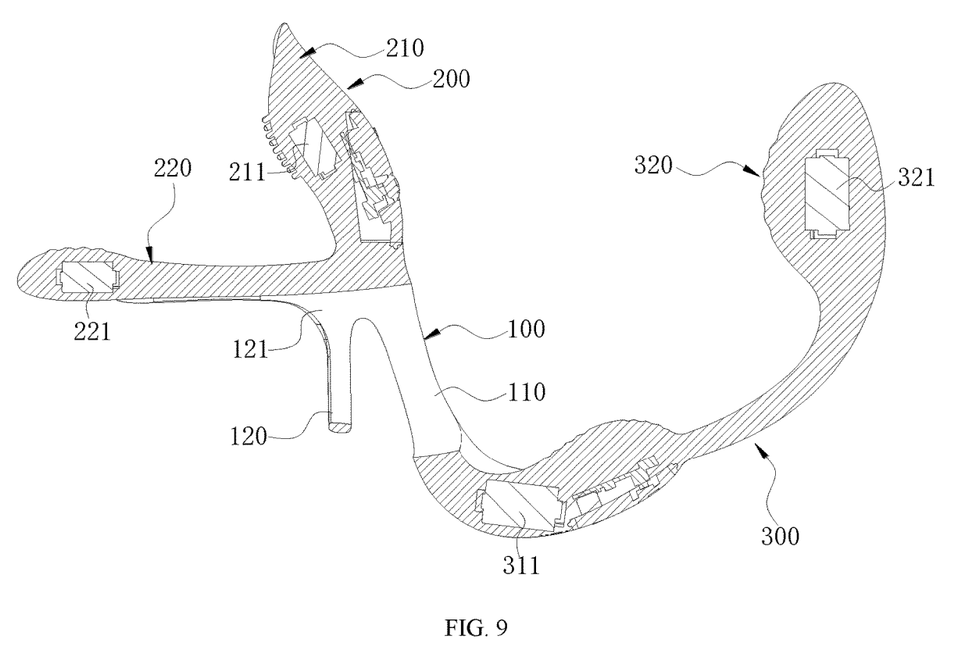

Referring to FIG. 7 to FIG. 9, in this embodiment, the ring structure 100 adopts the double-ring structure. The at least one first function member 200 includes a proximal first function member 210 and a distal first function member 220. The proximal first function member 210 is connected to the ring structure 100. The distal first function member 220 extends further from the proximal first function member 210. The stimuli provided by the distal first function member 220 include at least one of mechanical stimulus, electrical stimulus and heating stimulus. Particularly, the distal first function member 220 is connected to a front end of the proximal first function member 210 and extends in a forward direction. After the finger or the penis is inserted into the ring structure 100, the distal first function member 220 enters the vagina along with the finger or the penis, thus enabling the distal first function member 220 to stimulate the a sexually sensitive region at the anterior wall inside the vagina, namely, the G-spot. The stimuli provided to the vagina include at least one of mechanical stimulus, electrical stimulus and heating stimulus. When a male partner is about to wear the sexual stimulation device, the penis is aligned with the ring structure 100 and inserted into the ring structure 100. At this time, the distal first function member 220 conforms to the top of the penis. When the penis of the male partner is inserted into the vagina of the female, a side wall of a front side of the proximal first function member 210 abuts against the clitoris of the female partner and the area around the clitoris, and the distal first function member 220 enter the vagina together with the penis. When the stimulation source provided by each function member is energized, the proximal first function member 210 stimulates the clitoris of the female, and the distal first function member 220 stimulates the vagina of the female partner.

A second vibration stimulation source 221 is arranged within the distal first function member 220, such that after the second vibration stimulation source 221 is actuated, the distal first function member 220 can provide vibration massage to the vagina. Particularly, the second vibration stimulation source 221 may use a motor. It should be understood that since the distal first function member 220 conforms to the penis, and the distal first function member 220 can provide vibration massage to the penis, which can simultaneously provide the vibration massage for the male partner and the female partner. Preferably, threads are arranged on a top surface of one end of the distal first function member 220 away from the proximal first function member 210, which can improve the vibration massage effect.

Preferably, the distal first function member 220 is provided with an electrical stimulation source, which can provide an electrical stimulus sensation to the vagina and/or the penis. The electrical stimulation source can provide an electrical stimulus sensation to the vagina when being positioned on the top surface of distal the first function member 220. When the electrical stimulation sources are arranged on the top surface and the bottom surface of the distal first function member 220 and the ring structure 100 is mounted around the penis, the electrical stimulus may be simultaneously provided to the vagina and the penis. The electrical stimulation source in this embodiment includes a plurality of conductive members spaced from each other. The conductive members are spaced apart on the top surface of the distal first function member 220. In this way, the conductive members are in contact with the vagina, and the conductive members generate micro-currents, which provide an electrical stimulus sensation to the vagina. The second vibration stimulation source 221 is arranged within the distal first function member 220 and the electrical stimulation source is arranged on the top surface of the distal first function member 220, such that the distal first function member 220 can not only provide a vibration massage to the vagina and the penis, but also provide an electrical stimulus sensation to the vagina, which can make the male partner and the female partner reach excited states.

The at least one second function member 300 includes a proximal second function member 310 and a distal second function member 320. The proximal second function member 310 is connected to the ring structure 100. The distal second function member 310 extends further from the proximal second function member 320. Particularly, the proximal second function member 310 is connected to the bottom side of the ring structure 100 and extends backwards to stimulate the perineum of the male partner. The distal second function member 320 is connected to the rear end of the proximal second function member 310 and extends upwards. The distal second function member 320 is suitable for inserting into the anus of the male partner to stimulate the anus. A third vibration stimulation source 311 is arranged within the proximal second function member 310 and a fourth vibration stimulation source 321 is arranged within the distal second function member 320, such that the second function member 300 can provide vibration massage to the perineum and the anus of the male partner. Both the third vibration stimulation source 311 and the fourth vibration stimulation source 321 can use motors.

It should be understood that the first vibration stimulation source 210, the second vibration stimulation source 221, the third vibration stimulation source 311 and the fourth vibration stimulation source 321 can share a same circuit board, and function keys may be provided on the function member that is provided with the circuit board, and the corresponding vibration stimulation source may be turned on or off by pressing the corresponding function keys. The function keys can include an on/off key, a mode selection key and a power add-substrate key, which facilitates operation.

The sexual stimulation device may include a hard inner casing and a flexible outer casing, and the flexible outer casing surrounds the hard inner casing. All the vibration stimulation sources may use motors. The proximal first function member 210 may be designed to slightly inclined forwards, that is, the proximal first function member 210 is arranged to inclined forwards with respect to a vertical direction, such that after the male partner wears the sexual stimulation device, the proximal first function member 210 may abut against the clitoris area of the female partner.

The ring structure 100 includes a first sleeve 110 and a second sleeve 120 spaced from each other. The first sleeve 110 and the second sleeve 120 are both elastic and can extend and retract and deform radially, which is suitable for the male partner to wear. The first sleeve 110 is connected between the proximal first function member 210 and the proximal second function member 310. The second sleeve 120 is connected to one end of a bottom of the distal first function member 220 adjacent to the first sleeve 110. A gap is formed between the first sleeve 110 and the second sleeve 120. When the ring structure 100 is mounted around the penis, the penis passes through the first sleeve 110 and the second sleeve 120 sequentially. The second sleeve 120 plays a role of auxiliary fixation of the penis and makes the penis abut against the distal first function member 220. When the male partner wears the sexual stimulation device, the gap between the first sleeve 110 and the second sleeve 120 becomes smaller. The ring structure 100 has a function of blocking ejaculation, and the second sleeve 120 properly blocks the blood flow of the penis of the male partner, thereby increasing the volume and the stiffness of the penis. In this way, the ring structure 100 can effectively prolong the sexual duration. It should be understood that a plurality of second sleeves 120 that are spaced apart may be provided on the distal first function member 220.

An area of the distal first function member 220 between the first sleeve 110 and the second sleeve 120 may be in smooth transition. A joint between the second sleeve 120 and the bottom surface of the distal first function member 220 may be in smooth transition. Preferably, the width of the top end of the second sleeve 120 is greater than that of other areas, that is, the top end of the second sleeve 120 has a transition portion 121, and the width of the transition portion 121 gradually increases from top to bottom, such that strong structural strength between the second sleeve 120 and the distal first function member 220 is obtained. After the penis of the male partner is inserted into the ring structure 100, the distal first function member 220 may abut against the penis. Preferably, the front side and the rear side of the transition portion 121 extend to a side surface of the distal first function member 220, which can enhance the structural strength of the second sleeve 120 as well. The second sleeve 120 is difficultly pulled and damaged or fall off from the distal first function member 220 during the use.

Referring to FIG. 7 and FIG. 8, the overall dimension of the first sleeve 110 is set to be greater than that of the second sleeve 120. That is, the inner diameter of the first sleeve 110 is set to be greater than the inner diameter of the second sleeve 120, such that the scrotum will not extend into the first sleeve 110 when the penis passes through the first sleeve 110.

The first sleeve 110 is inclined backwards with respect to a longitudinal axis P of the distal first function member 220. The first sleeve 110 is substantially perpendicular to the longitudinal axis P of the distal first function member 220, such that the first sleeve 110 is inclined with respect to the second sleeve 120, and the penis is more stable and unlikely to fall off after being inserted into the ring structure 100.

Figure 10:
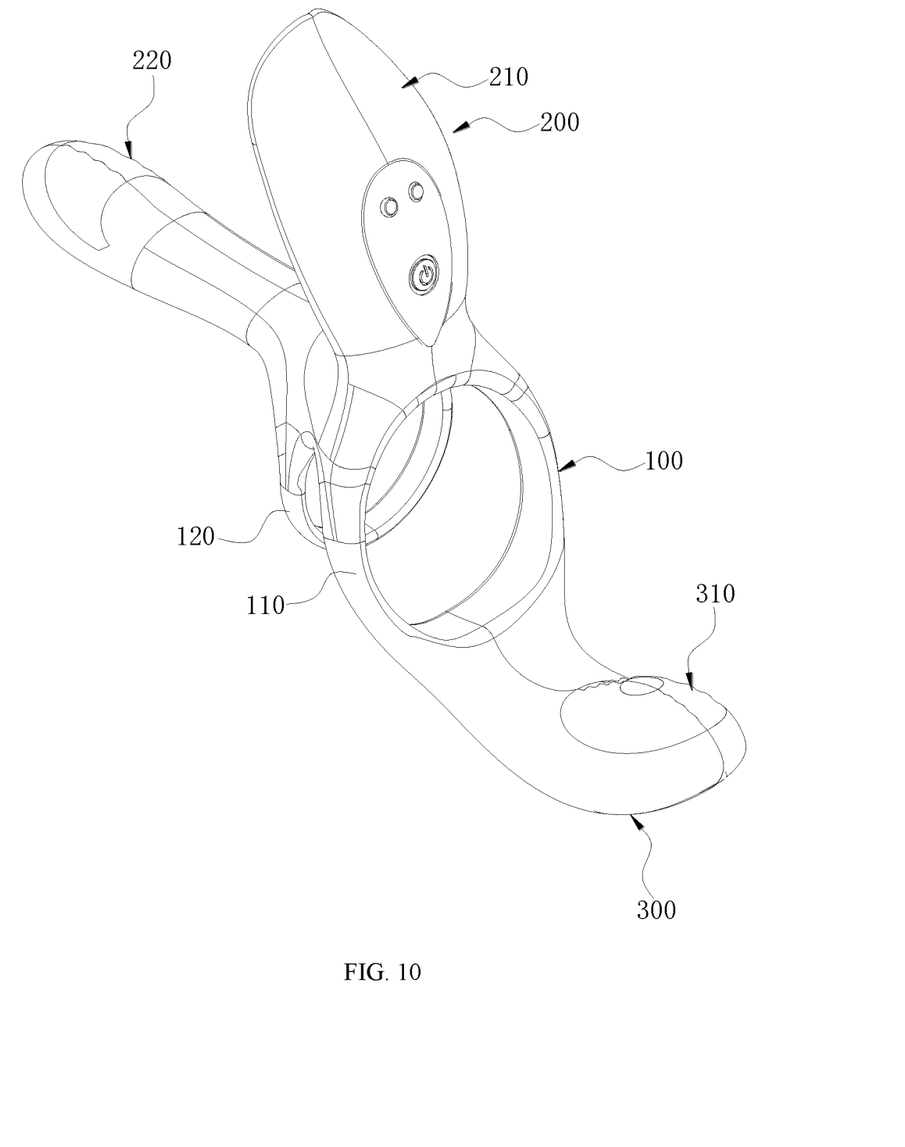
FIG. 10 is a perspective view showing a sexual stimulation device in accordance with a further embodiment of the present invention.
Figure 11:
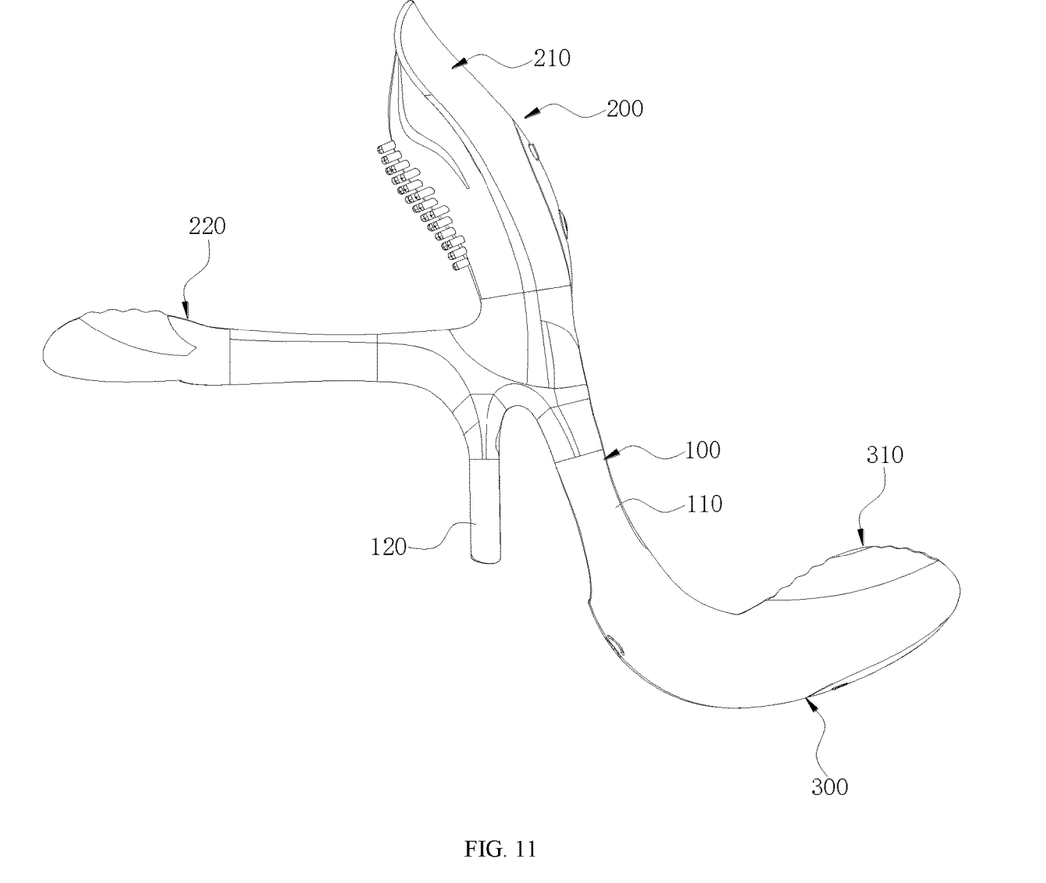
FIG. 11 is a side view of the sexual stimulation device shown in FIG. 10.

Referring to FIG. 10 and FIG. 11, in this embodiment, the ring structure 100 adopts the double-ring structure. The at least one first function member 200 includes a proximal first function member 210 and a distal first function member 220. The at least one second function member 300 includes a proximal second function member 310. The ring structure 100 includes a first sleeve 110 and a second sleeve 120 spaced from each other. The proximal second function member 310 is used to stimulate the perineum of the male partner. The distal first function member 220 is connected to the front end of the first function member 200 and extends in a forward direction. After the penis of the male partner is inserted into the ring structure 100, the distal first function member 220 enters the vagina along with the penis, thereby stimulating the vagina. The first vibration stimulation source is arranged within the proximal first function member 210, the second vibration stimulation source is arranged within the distal first function member 220, and the third vibration stimulation source is arranged within the proximal second function member 310. After the male partner wears the sexual stimulation device, the vibration massage may be generated on the perineum of the male partner, the vagina of the female partner, the clitoris and the area around the clitoris.

Figure 12:
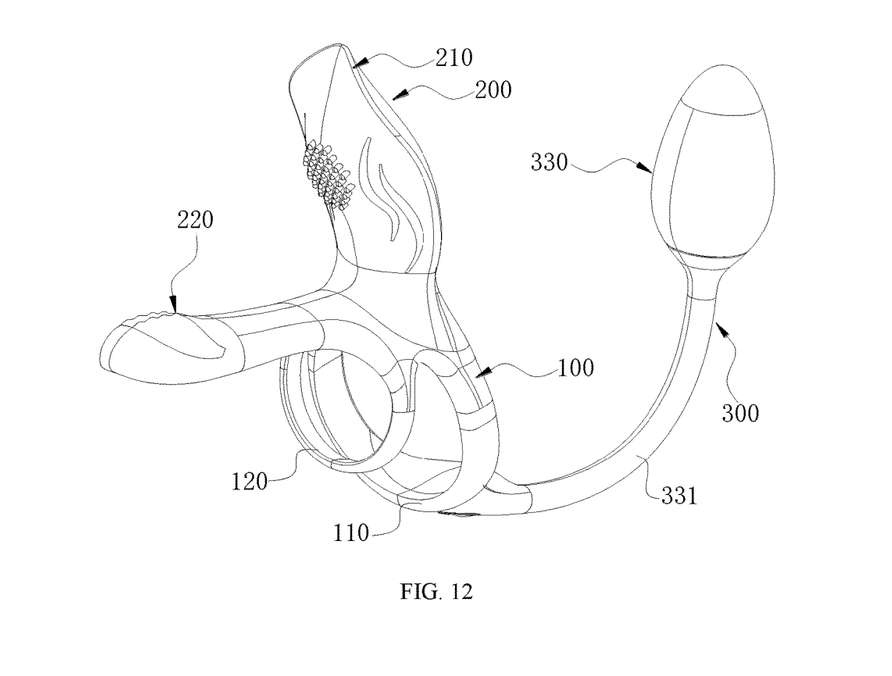
FIG. 12 is a perspective view showing a sexual stimulation device in accordance with a further embodiment of the present invention.
Figure 13:
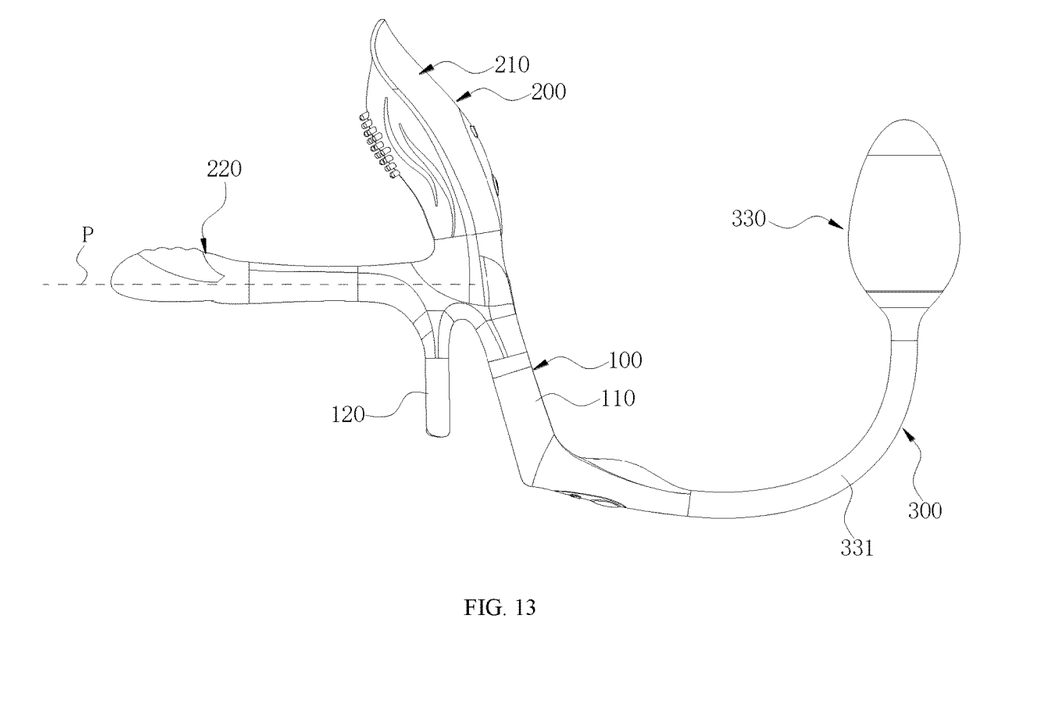
FIG. 13 is a side view of the sexual stimulation device shown in FIG. 12

Referring to FIG. 12 and FIG. 13, in this embodiment, the ring structure 100 adopts the double-ring structure. The at least one first function member 200 includes a proximal first function member 210 and a distal first function member 220. The at least one second function member 300 includes an anal plug 330. The ring structure 100 includes a first sleeve 110 and a second sleeve 120 spaced from each other. The distal first function member 220 is connected to the front end of the proximal first function member 210 and extends in a forward direction. After the penis of the male partner is inserted into the ring structure 100, the distal first function member 220 enters the vagina along with the penis, thus stimulating the vagina. The anal plug 330 is suitable for inserting into the anus of the male partner to stimulate the anus. The anal plug 330 is connected to the ring structure 100 through the connecting member 331. The width of the connection region of the connecting member 331 to the ring structure 100 gradually decreases from the front side to the rear side. The remaining portion of the connecting member 331 is of the elongated and curved column shape. The first sleeve 110 is inclined backwards with respect to the longitudinal axis P of the distal first function member 220, and the proximal first function member 210 is inclined forwards with respect to the longitudinal axis P of the distal first function member 220.

The sexual stimulation device of the present invention may be equipped with a remote control, such that the sexual stimulation device may be controlled in a wireless remote control manner. Alternatively, the sexual stimulation device of the present invention may be further provided with a communication module, which can achieve a wireless connection with a mobile terminal. The user can control the sexual stimulation device remotely through a mobile phone, a tablet and other applications on the mobile terminal, which can improve the convenience of use.

It should be understood that each function member of the sexual stimulation device of the present invention may be configured with different or the same stimulation sources, such as mechanical stimulus sources, electrical stimulation sources, and heating stimulation sources. The user can turn on or off some of the stimulation sources according to their own needs, which can provide users with more choices, enrich the functions of the sexual stimulation device, and improve the adaptability.

The above are only preferable embodiments of the present invention and are not intended to limit the present invention. Any modification, equivalent replacements and improvements made within the spirit and principle of the present invention shall be included in a scope of protection of the present invention.

The invention claimed is:
1. A sexual stimulation device, comprising:
a ring structure;
at least one first function member positioned at one side of the ring structure;
at least one second function member positioned at an other side of the ring structure; and
at least one battery arranged in the first function member and/or the second function member,
wherein the first function member and the second function member collectively comprise N stimulation sources, and wherein N is greater than or equal to 3;
wherein the at least one first function member comprises a proximal first function member and a distal first function member connected to the ring structure;
wherein the ring structure comprises a first sleeve and a second sleeve spaced from each other, the first sleeve being connected between the proximal first function member and the at least one second function member, and the second sleeve is connected to a bottom of the distal first function member and is adjacent to one end of the first sleeve.

2. The sexual stimulation device of claim 1, wherein stimuli provided by the N stimulation sources comprise at least one of the following: mechanical stimulus, electrical stimulus and heating stimulus.

3. The sexual stimulation device of claim 2, wherein the mechanical stimulus is at least one of the following: vibrating, swinging, twisting, buckling, slapping, extending-retracting and suctioning.

4. The sexual stimulation device of claim 1, wherein the proximal first function member is provided with a first on/off key.

5. The sexual stimulation device of claim 1, wherein a vibration stimulation source is arranged within the proximal first function member.

6. The sexual stimulation device of claim 1, wherein a vibration stimulation source is arranged within the distal first function member.

7. The sexual stimulation device of claim 1, wherein the distal first function member is provided with an electrical stimulation source.

8. The sexual stimulation device of claim 1, wherein a diameter of the first sleeve is larger than a diameter of the second sleeve.

9. The sexual stimulation device of claim 1, wherein the first sleeve is inclined backwards with respect to a longitudinal axis of the distal first function member.

10. The sexual stimulation device of claim 1, wherein a top end of the second sleeve has a transition portion, and a width of the transition portion gradually increases from top to bottom.

11. The sexual stimulation device of claim 10, wherein a front side and a rear side of the transition portion extend to side surfaces of the distal first function member, respectively.

12. The sexual stimulation device of claim 1, wherein the at least one second function member comprises a proximal second function member for stimulating a testis and/or a perineum, and the proximal second function member is connected to the ring structure.

13. The sexual stimulation device of claim 12, wherein the proximal second function member is provided with an on/off key.

14. The sexual stimulation device of claim 12, wherein a vibration stimulation source is arranged within the proximal second function member.

15. The sexual stimulation device of claim 12, wherein the at least one second function member further comprises a distal second function member configured for inserting into an anus, and the distal second function member being connected to one end of the proximal second function member away from the ring structure.

16. The sexual stimulation device of claim 15, wherein a vibration stimulation source is arranged within the distal second function member.

17. The sexual stimulation device of claim 1, wherein the at least one second function member comprises an anal plug for inserting into an anus, and the anal plug is connected to the ring structure through a connecting member.

* * * * *